US006261306B1

(12) United States Patent
Kramer

(10) Patent No.: US 6,261,306 B1
(45) Date of Patent: Jul. 17, 2001

(54) ACUPRESSURE TREATMENT DEVICE

(75) Inventor: George Henry Kramer, Minnetonka, MN (US)

(73) Assignee: East West Medical L.L.P., Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/487,838

(22) Filed: Jan. 19, 2000

Related U.S. Application Data

(63) Continuation of application No. 09/177,215, filed on Oct. 22, 1998, now Pat. No. 6,030,408.

(51) Int. Cl.$^7$ .............................. A61B 17/00
(52) U.S. Cl. .............................. 606/204
(58) Field of Search .............................. 606/204, 201, 606/189; 128/303; 604/116

(56) References Cited

U.S. PATENT DOCUMENTS

| | | | | |
|---|---|---|---|---|
| 3,866,597 | | 2/1975 | Boxer | 128/1 R |
| 3,886,939 | | 6/1975 | Boxer | 128/268 |
| 3,901,234 | * | 8/1975 | Yazawa | 128/268 |
| 3,987,787 | | 10/1976 | Boxer | 128/1 R |
| 4,022,189 | | 5/1977 | Boxer | 128/1 R |
| 4,073,296 | | 2/1978 | McCall | 128/303 |
| 4,098,277 | | 7/1978 | Mendell | 128/303 R |
| 4,391,270 | * | 7/1983 | Uragami | 128/1.3 |
| 5,250,067 | * | 10/1993 | Gelfer et al. | 606/189 |
| 5,366,475 | | 11/1994 | Voss et al. | 606/204 |
| 5,405,357 | * | 4/1995 | Rowe-Lanzisera et al. | 606/204 |
| 5,735,143 | | 4/1998 | Tanaka | 63/14.3 |
| 5,792,176 | * | 8/1998 | Chang | 606/204 |
| 6,030,408 | * | 2/2000 | Kramer | 606/204 |

FOREIGN PATENT DOCUMENTS

| | | | |
|---|---|---|---|
| 0100050 | 2/1984 | (EP) | A61H/39/00 |
| 11042268 | 2/1999 | (JP) | A61H/39/04 |

OTHER PUBLICATIONS

National Institutes of Health Consensus Development Conference Statement, 107. Acupuncture, http://odp.od.nih.gov/consensus, pp. 1–30, (Nov. 3–5, 1997).

* cited by examiner

*Primary Examiner*—Henry J. Recla
*Assistant Examiner*—William Lewis
(74) *Attorney, Agent, or Firm*—Schwegman, Lundberg, Woessner & Kluth, P.A.

(57) ABSTRACT

An acupressure device for use on a selected skin surface portion of a human body. The device comprises a thin flexible base sheet having a first side, a second side and a margin. The margin has at least a portion of its length shaped as an orienting margin, wherein the orienting margin is shaped to correspond to a shape on, or adjacent to, the selected skin surface portion when the base sheet is placed on the selected body surface. An adhesive layer is on the first side of the base sheet that is suitable for attaching the base sheet to the selected skin surface portion. There is at least one bead on the adhesive layer suitable for positioning against the selected body surface that will provide acupressure to at least a portion of the selected body surface when the acupressure patch is placed against the selected body surface.

18 Claims, 7 Drawing Sheets

ACUPRESSURE TREATMENT DEVICE

This application is a Continuation of U.S. application Ser. No. 09/177,215 filed Oct. 22, 1998, now U.S. Pat. No. 6,030,408.

FIELD OF THE INVENTION

The present invention relates to an acupressure device, and, in particular, to an acupressure device having a shaped peripheral margin shaped to key to specific landmarks of the human body.

BACKGROUND OF THE INVENTION

Acupressure, as with acupuncture, is a form of treatment for various conditions and maladies. Acupuncture is well known to eastern medical thought and practice, but only recently is introduced into western medicine. Acupuncture can be traced back at least 2,500 years as a form of medical treatment in China. The concept behind acupuncture is based on the premise there are patterns of energy flow through the body that are essential for proper health. Imbalance or disruption of energy flow through any of these patterns is believed to be responsible for disease. Which pattern is disrupted, and where, influences which disease state is experienced by the afflicted person.

The energy flow patterns through the body have been mapped extensively and there are substantial numbers of points along the flow patterns where the energy flow is close to the skin surface. Using needles of various types, the acupuncturist is able to reach these points by placing the needles into the skin at these known points. The presence of the needle at that point alters the flow of energy, changing the dynamics in the energy flow. When done properly, using the proper number and position of needles, acupuncture re-aligns the energy flow to one of balance and restoration of health.

The pattern of energy flow disruption is identifiable to the type of disease that the patient presents with. The acupuncturist determines the ailment complained of which then identifies the energy flow imbalance. The energy flow imbalance is then corrected by placing one or more needles into the appropriate points that are associated with the type of energy flow imbalance corresponding to the disease.

The National Institutes of Health Consensus Development Statement on Acupuncture, No. 107, Nov. 3–5, 1997, concluded that acupuncture was an effective therapy for certain medical conditions, especially those involving nausea and pain and should be integrated into standard medical practice. In particular, headaches, nausea, menstrual cramps, low back pain and dental analgesia were some of the medical conditions acupuncture was considered useful for.

The most common use for acupuncture in the U.S. is pain, with headache as the most frequent complaint in doctors' offices review of symptoms, and the most frequent reason for use of over-the-counter medications. U.S. and Chinese studies have shown acupuncture and acupressure therapy useful for pain and headache in particular. The use of acupressure therapy for headaches in the hands of the lay public could greatly enhance the treatment of headaches by a simple inexpensive technique with virtually no negative side effects.

Acupressure is a direct offshoot of acupuncture wherein one or more known points on the surface of the skin receive pressure instead of having a needle inserted. The concept remains the same, re-institute balanced energy flow as treatment of a malady caused by an imbalance in the energy flow through the body.

Acupuncture and acupressure points are at anatomically defined areas of the skin along 12 meridians, or lines of energy flow. In addition, further research has determined that there are several areas on the surface of the skin where the entire body is represented as a homunculus. Several areas incorporating a homunculus representation are the ears, hands, and soles of the feet. Acupuncture and acupressure to portions of the ear, hand, or sole of the foot effects a corrective energy change in the part of the body represented by that part of the homunculus.

Several acupressure devices are known in the art. A few are U.S. Pat. Nos. 3,866,597; 3,886,939; 3,987,787; and 4,022,189, and all issued to Boxer. The devices disclosed make use of one or more small rigid objects that are applied by the user to one or more particular points of the user's body. The devices disclosed are either square or rectangular in shape and they either have a single small object in the center or several spread randomly across the surface of the device. Each of these devices requires that either the user or a helper have considerable knowledge and experience in determining where and how to place the objects on the user's skin. U.S. Pat. No. 3,901,234 issued to Yazawa discloses a similar device to that of Boxer, but adds a medicated adhesive layer.

U.S. Pat. No. 4,098,277 issued to Mendell discloses a custom molded, and expensive, device for use in a person's ear that bears one or more blunt protrusions of the mold surface as acupressure points. Such a device is limited to use by only the person for which the device is molded and requires skilled help in fabricating the device. Placement of the acupressure points on the device is permanent. A single patient would require any number of individual custom molded devices, each device having a different pattern of acupressure points corresponding to treatment of differing maladies, in order to treat the different maladies that one person may encounter over time.

Another device is disclosed in U.S. Pat. No. 4,073,296 issued to McCall wherein the device is a custom molded piece, again for a single individual's ear. This device incorporates nodules inserted into the surface of the molded device to achieve the acupressure effect. Like the Mendell device, this device requires one of high skill to construct the device for proper fit and each mold can only treat the one specific malady intended.

What is needed is a device that is relatively inexpensive and easy enough to be applied by the user without need to involve an expert in acupressure in the process. The device will conform and mold easily to the user's skin surface. Different shapes of the device would have uses outside of just placement on, or about, the user's ear. Each shape will be keyed to a particular anatomical surface shape that is readily identifiable to the user, thus providing easy accurate placement of the acupressure device.

SUMMARY OF THE INVENTION

The present invention discloses an acupressure device for use on a selected skin surface portion of a human body. The device comprises a thin flexible base sheet having a first side, a second side and a margin. The margin has at least a portion of its length shaped as an orienting margin, wherein the orienting margin is shaped to correspond to a shape on, or adjacent to, the selected skin surface portion when the base sheet is placed on the selected body surface. An adhesive layer is on the first side of the base sheet that is suitable for attaching the base sheet to the selected skin surface portion. There is at least one bead on the adhesive layer suitable for positioning against the selected body surface that will provide acupressure to at least a portion of the selected body surface when the acupressure patch is placed against the selected body surface.

An object of the present invention is to provide a device that may be applied by any user with out any need for formal training in acupressure treatment or anatomy. Such a device anticipates construction with materials that are medically approved and hypoallergenic.

Another object of the present invention is to provide a device that is capable of adapting to a number of different treatments. This is accomplished by using any number of beads, in any number of different patterns, appropriate for any number of individual maladies and pains. The various different numbers of patterns are keyed to the corresponding orienting margins, which are then alignable to the appropriate anatomical landmark. This is to ensure that the proper treatment is applied to the proper skin area corresponding to the anatomical landmark.

These and other objects of the present invention and many of the attendant advantages of the present invention will be readily appreciated as the same become better understood by reference to the following detailed description when considered in connection with the accompanying drawings.

DETAILED DESCRIPTION OF THE INVENTION

Figure 1:
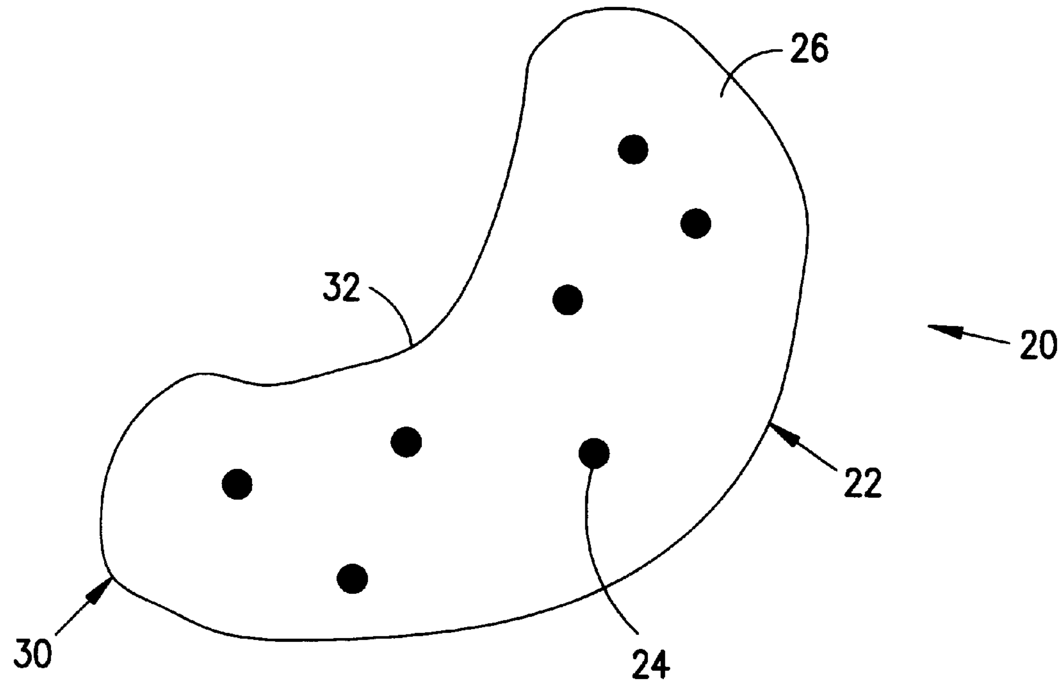
FIG. 1 is a bottom plan view of an embodiment of the present invention.
Figure 2:
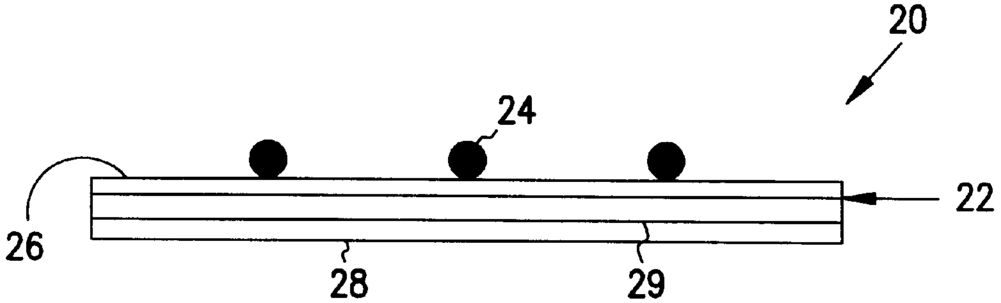
FIG. 2 is a side elevational view of the embodiment depicted in FIG. 1.

In reference to the various Figures, wherein like reference numbers refer to like components throughout the various Figures, there is disclosed an embodiment of the present invention is depicted in FIGS. 1 and 2 as an acupressure patch 20 comprising a base sheet 22 and at least one bead 24. Base sheet 22 includes an adhesive layer 26, an opposite outer surface 28 and a peripheral margin 30. Peripheral margin 30 includes an orienting margin 32 that is at least a portion of peripheral margin 30. Not depicted is a release film placed over adhesive layer 26 and at least one bead 24 at the time of manufacture. The purpose of a release film is to provide for convenient packaging and to prevent premature, inadvertent or undesired application of acupressure patch 20. The types and uses of release films are well known in the art.

Base sheet 22 therefore may be manufactured from a number of different materials ranging from a cloth to a film. Various cloths useful as a base sheet include weaves made from synthetic or natural fibers, or a blend of both. Useful fibers include cotton, Dacron, polyester, and nylon. Alternatively, the base sheet may be a film made from natural or synthetic polymers and copolymers including cellulose, cellulose acetate, polyurethane, polyvinyl chloride, polyester, polypropylene, polyethylene, polytetrafluoroethylene, and various silicones and siloxane polymers. The film may be also be a foamed plastic. Preferably, the material used for base sheet 22 is of medical grade material desirable for its biocompatibility and is hypoallergenic.

The at least one bead 24 may include any number of beads from one to greater than ten, or even twenty beads arranged in a pattern intended for any number of possible treatment patterns, examples of which are to be explained below. Spacing of the beads is also dependent on the intended therapy and the site of on the skin the acupressure patch is to be placed. The size of the beads may vary in diameter from less than about 0.5 mm to greater than about 2 mm.

The beads may be manufactured from a number of different materials including metals, metal alloys, various ceramics and glasses, hard rubbers, and hard polymers. Useful metals include iron, stainless steel, nickel, copper, tin, zinc, platinum, gold and silver, and the various alloys attainable with these metals. A choice of metal or metal alloy may also depend on whether it is desired to include magnetic therapy using a magnetized metal or alloy with the use of the acupressure patch.

Adhesive layer 26 may be constructed from various adhesives in the form of pressure sensitive adhesives that are well known to the art. Choice of an appropriate adhesive is guided by a desire to provide a medical grade, biocompatible, and hypoallergenic adhesive with good adhesive quality. Adhesive layer 26 is also useful in adhering at least one bead 24 to base sheet 22.

Figure 3:
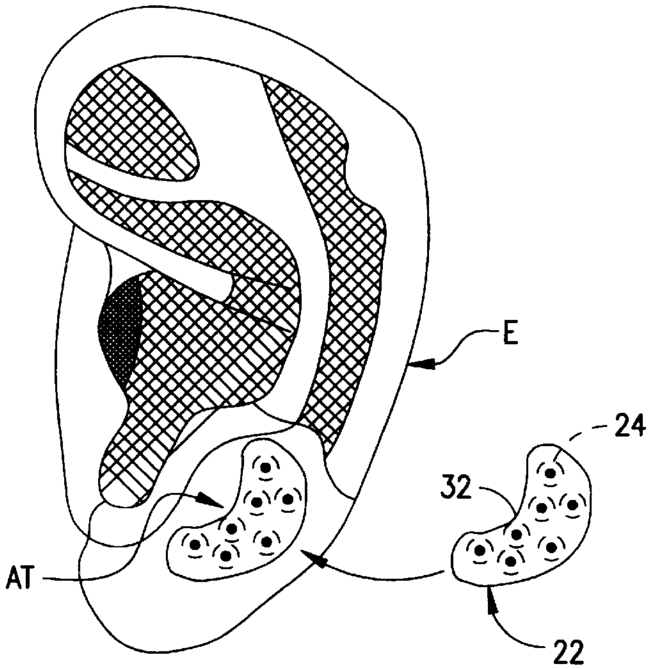
FIG. 3 is a top plan view of the embodiment depicted in FIG. 1 showing the relationship of the device to a specific anatomic landmark.
Figure 4:
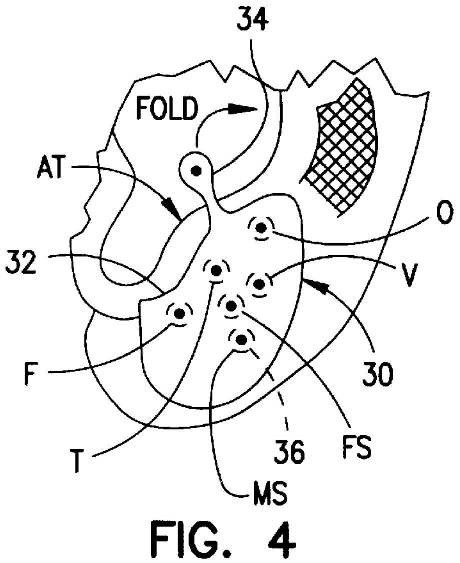
FIG. 4 is a top plan view of an alternative embodiment of the present invention shown in relationship to a specific anatomic landmark.

Peripheral margin 30 includes at least a portion of peripheral margin 30 as orienting margin 32. The present invention contemplates the use various surface anatomic landmarks adjacent to known meridian points and homunculus representations to shape orienting margin to conform to the various surface anatomic landmarks of interest. By way of example, it is known that a person's head is represented on a portion of the person's pinna very near the anatomic landmark identified as the antitragus (AT in the various Figures) The points of interest to the head correspond to therapy points used in acupressure to promote relief from headache occurring in those areas of the head so represented. This pattern of representation and the pattern's spatial relationship to the antitragus is uniform from one person to the next. Therefore, orienting margin 32 may be shaped to contour the base of the antitragus, and at least one bead 24 may be positioned on base sheet 22 relative to orienting margin 32 to correspond to at least one therapy point in the vicinity of the antitragus. Just such an example using six known therapy points is depicted in FIG. 4 therefore As shown in FIG. 4 therefore, on the outer surface of a person's pinna near the antitragus and just superior to the lobe of the pinna there are represented at least six ipsilateral areas of the corresponding skull. These six areas are frontal skull F, temporal skull T, occipital skull O, vertex of skull V, frontal sinus FS, and master sensorial MS. Note the spatial relationship of these six areas to the antitragus. As shown in FIG. 3, Orienting margin 32 is shaped to conform to the outline of the base of the antitragus and six beads 24 are positioned across the surface of base sheet 22 to correspond to the six areas of the skull. When the user positions orienting margin 32 to conform to the base of the antitragus, the six beads 24 will then align with the six areas of the skull represented there on the surface of the pinna. Thus, even a user untrained in the art of acupressure successfully accomplishes acupressure therapy.

Figure 5:
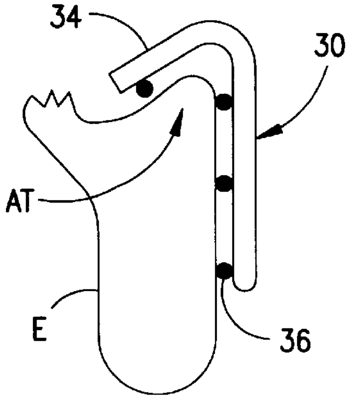
FIG. 5 is a side elevational view of the embodiment depicted in FIG. 4 shown in position in relationship to a specific anatomic landmark.

FIG. 4 depicts a variation of the embodiment of the present invention wherein orienting margin 32 extends an accessory lobe 34 to an adjacent therapy point. In this example, accessory lobe 34 is extended to the therapy point on the inner surface of the pinna representing area subcortex SC by folding accessory lobe 34 over the rim the anithelix of the pinna to reach SC. FIG. 5 shows a side elevational view depicting how this positioning is accomplished.

Figure 6:
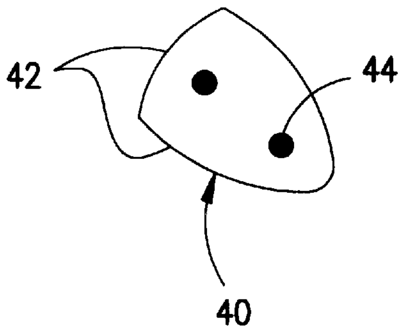
FIG. 6 is a bottom plan view of an additional alternative embodiment of the present invention.
Figure 7:
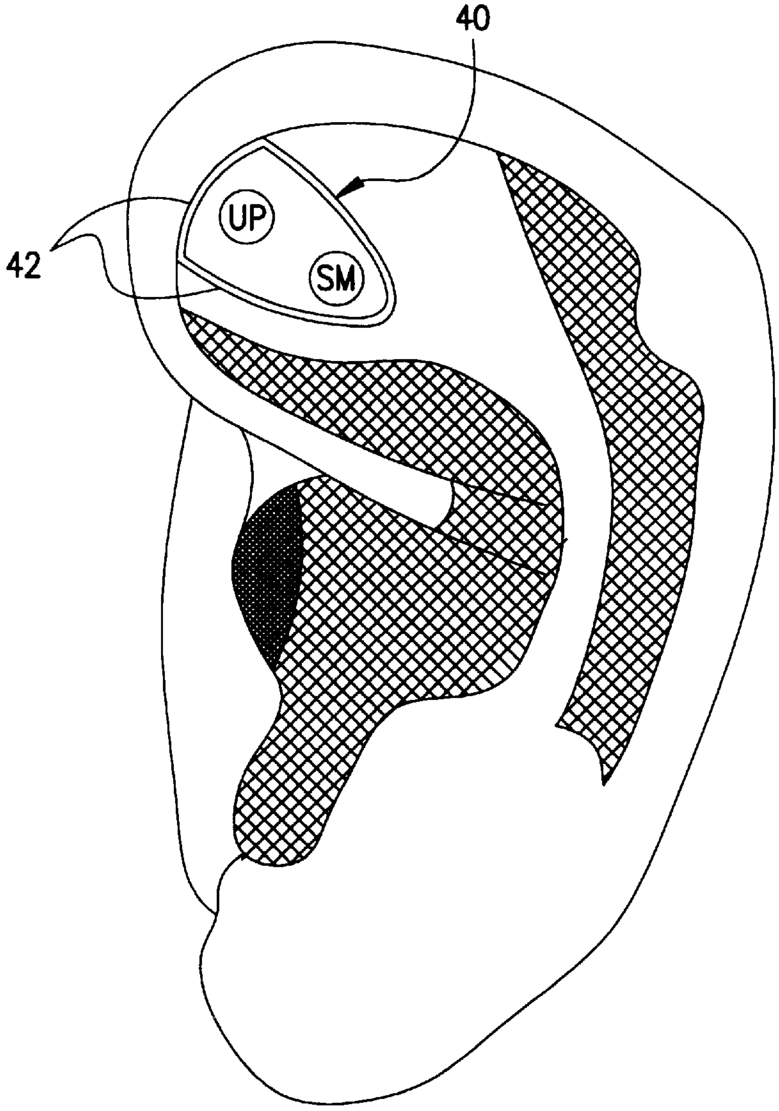
FIG. 7 is a top plan view of the embodiment depicted in FIG. 6 shown in relationship to a specific anatomic landmark.

A majority of the surface of a person's pinna represents the body in the form of a homunculus. As noted above, various areas of a person's ipsilateral skull area represented by therapy points proximate the antitragus. FIG. 6 discloses an acupressure patch 40 having an orienting margin 42 and at least one bead 44. In FIG. 7, there is shown the representative points of the body for the uterus point UP and the shen men SM which are found near the inner margin of the helix. Acupressure patch 40 is positioned with orienting margin 42 adjacent the inner margin of the helix to position beads 44 over the therapy points UP and SM.

Figure 9:
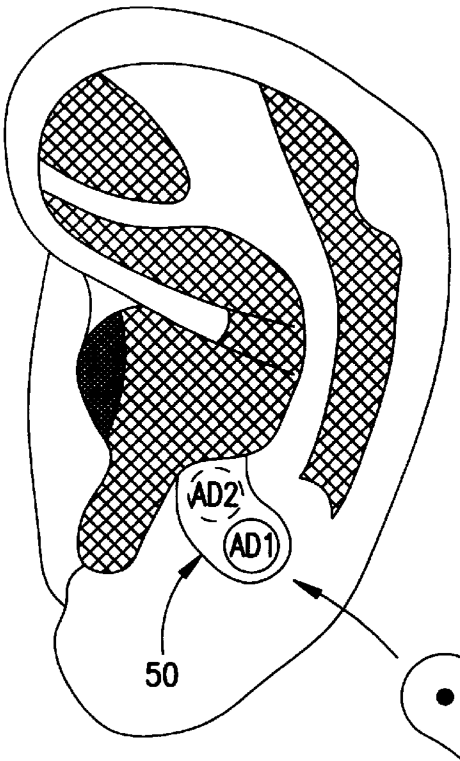
FIG. 9 is a partial plan view of the embodiment depicted in FIG. 8 shown wrapping over a specific anatomic landmark.
Figure 8:
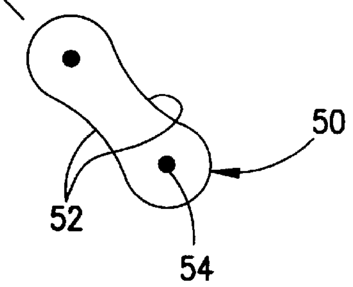
FIG. 8 is a bottom plan view of another additional alternative embodiment of the present invention.
Figure 10:
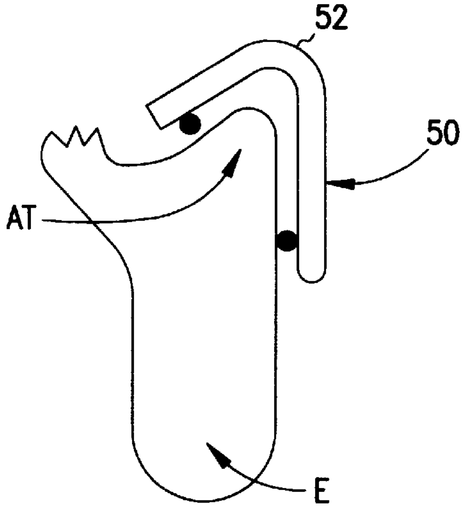
FIG. 10 is a side elevational view of the embodiment of FIG. 8 shown in relationship to a specific anatomic landmark.

Another example is depicted in FIGS. 8–10 disclosing an acupressure patch 50 having an orienting margin 52 in the shape of a wasp waste and at least one bead 54. Represented on the surface of a person's pinna are two antidepressant areas AD1 and AD2. These two areas are opposite each other over the rim of the antihelix proximate the point where the antihelix meets the edge of the antitragus. Orienting margin 52 fits within the hollow found at the junction between the antihelix and antitragus thus positioning acupressure patch 50 and its associated beads 54 over therapy points 1 and 2.

Also contemplated by the present invention, as depicted in FIG. 2, is the addition of a layer of medicament 29 or a medicament that can be mixed or blended into the base sheet material. The layer may be to either surface of the base sheet depending on the material used in the base sheet and film versus weave construction. The medicament is then available to the wearer of the device, for absorption through their skin, as an additional adjunct to the acupressure effects provided by the at least one bead. Examples of useful medicaments include camphor, tiger balm, wintergreen or other pharmacological agents for transdermal or topical use.

Figure 11:
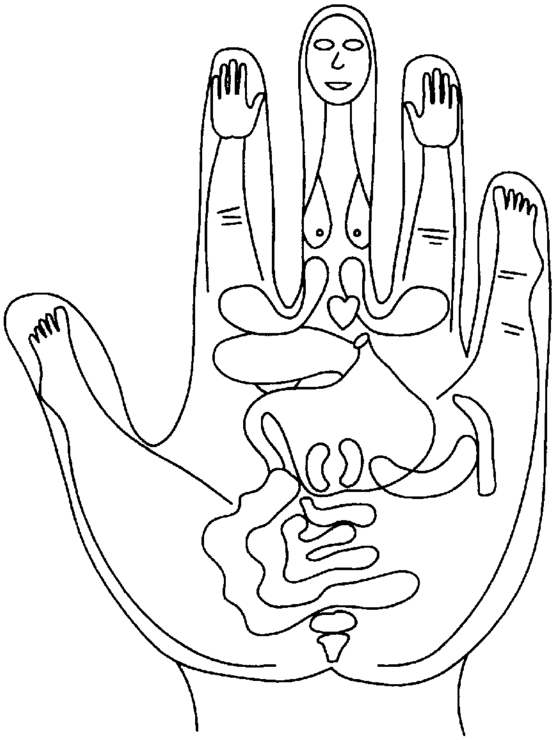
FIG. 11, for reference, depicts a ventral view of a homunculus representation found on the palmar surface of a human hand.
Figure 12:
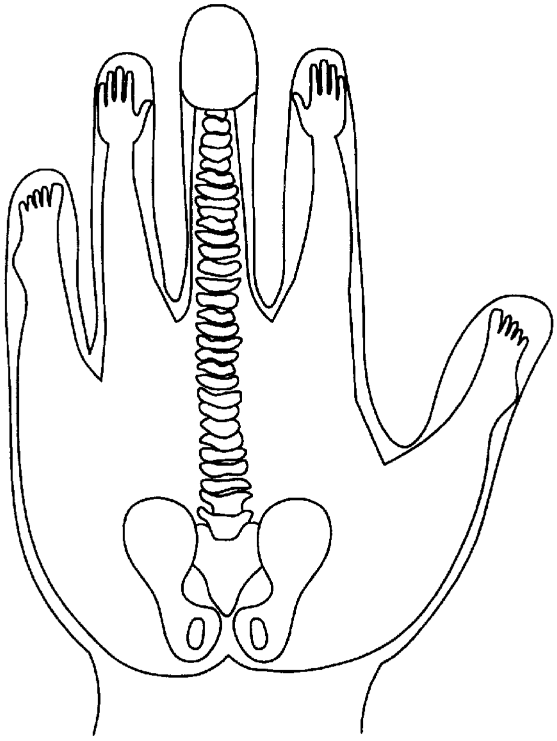
FIG. 12, for reference, depicts a dorsal view of a homunculus representation found on the dorsal surface of a human hand.

The previous description is exemplary of a few of the many embodiments contemplated by the present invention for use on or about the ear (E). The use of an orienting margin can be extended to any surface area of the human body. For example, as shown diagrammatically in FIGS. 11 and 12, the body is represented in homunculus form on the surface of the hand. In FIG. 11, on the palmar surface one notes the representation of the ventral surface and internal organs of the human. In FIG. 12, the dorsal aspect of the body is represented on the extensor surface of the hand. These maps are uniform from one person to the next. The present invention, using the orienting margin concept, provides for any number of acupressure patches that can be placed accurately, and reproducibly, by anyone regardless of level of skill in the art of acupressure.

Figure 13:
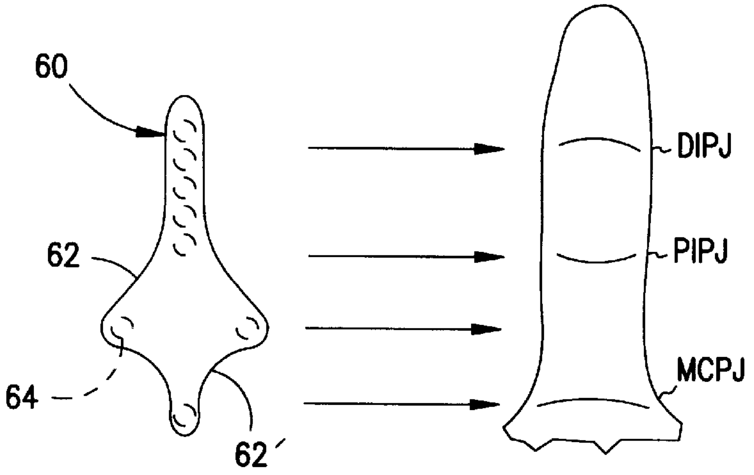
FIG. 13 depicts a top plan view of a further additional embodiment of the present invention aligned with a specific anatomic relationship as shown by the arrows as to where the device is to be placed on the skin.

FIGS. 13–16 depicted representative examples of the various types of embodiments contemplated by the present invention for exploiting the known acupressure and acupuncture sites on the human body. FIG. 13 depicts an acupressure patch 60 having an orienting margin 62,62' and at least one bead 64 shown in phantom as being on the other side of acupressure patch 60. Such an acupressure patch is useful for placing beads in a pattern for treating anterior portions of the head, face, neck and upper chest. The pattern of beads used is variable, depending on the area of the body desired to be treated by acupressure to the equivalent homunculus area, and is not a limiting factor in the present invention. Orienting margin 62,62' is used to align acupressure patch 60 to the user's finger. In FIG. 13, orienting margin 62,62' is used to align acupressure patch 60 so orienting margin 62,62' is between the user's metacarpophalangeal joint MCPJ and the proximal interphalangeal joint PIPJ. The several arrows show how the device is moved into place relative to the MCPJ, PIPJ and the distal interphalangeal joint DIPJ. The long axis of acupressure patch 60 is aligned along the midline of the finger.

Figure 14:
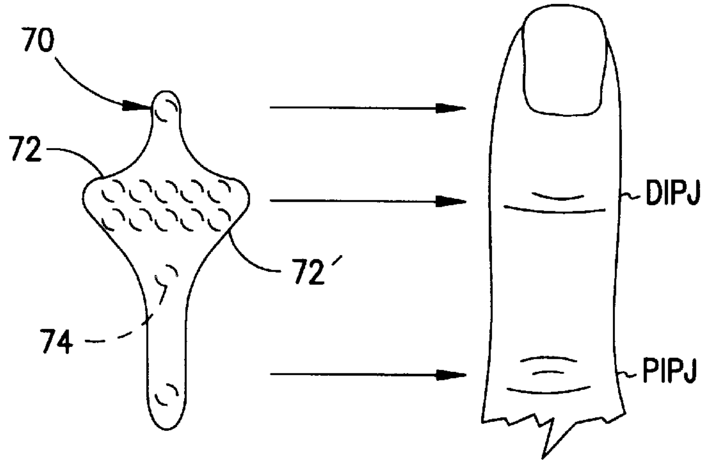
FIG. 14 depicts a top plan view of an another further additional embodiment of the present invention aligned with a specific anatomic relationship as shown by the arrows as to where the device is to be placed on the skin.

FIG. 14 depicts an acupressure patch 70 as an embodiment of the present invention useful for treating disorders associated with the back of the head and spine. Acupressure patch 70 includes an orienting margin 72,72' and at least one bead 74. In this embodiment, orienting margin 72,72' is aligned with the plane of the DIPJ on the extensor surface of the user's finger and the long axis of acupressure patch 70 is aligned along the midline of the finger.

Figure 15:
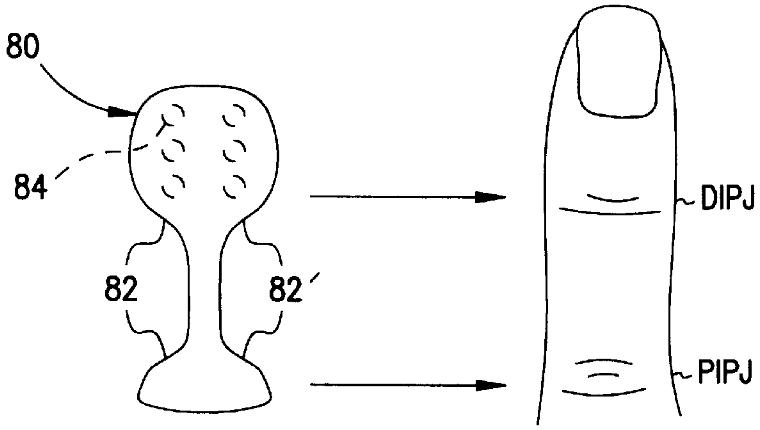
FIG. 15 depicts a top plan view of yet another further additional embodiment of the present invention aligned with a specific anatomic relationship as shown by the arrows as to where the device is to be placed on the skin.

FIG. 15 depicts another variation of an embodiment of the present invention as an acupressure patch 80 having an orienting margin 82,82' and at least one bead 84. Orienting margin 82,82' is aligned between two joints, in this example between the PIPJ and the DIPJ. The long axis is again aligned with the midline of the finger.

Figure 16:
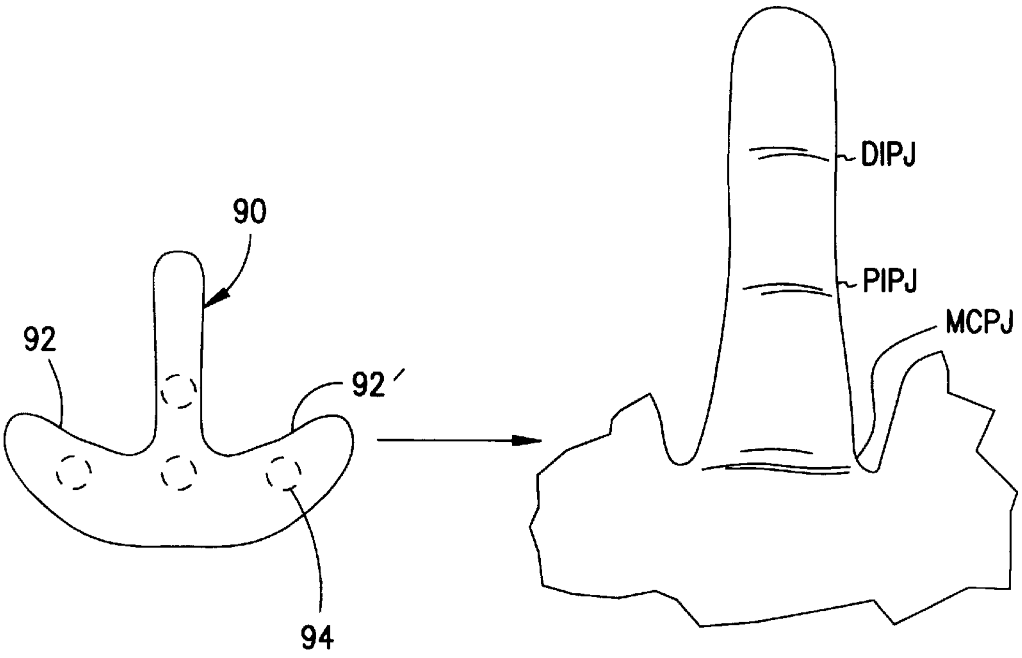
FIG. 16 depicts a top plan view of yet another further additional embodiment of the present invention aligned with a specific anatomic relationship as shown by the arrows as to where the device is to be placed on the skin.

FIG. 16 depicts an acupressure patch 90 having an orienting margin 92,92' and at least one bead 94. This embodiment depicts one use of an orienting margin for obtaining alignment of an acupressure patch to the contours of a user's palm. Orienting margin 92,92' is used to align acupressure patch 90 along the midline of a digit, to the MCPJ of that digit, and to the web areas between the digit and the two digits to either side.

There are other areas, including homunculus equivalent areas, elsewhere on the surface of a body. In particular, there are twelve meridians and the homunculi of the feet and nose may also be approached for treatment with a device of the present invention. The number of possible embodiments is extensive and overly burdensome to depict and describe each and every one. The principles of the present invention have been presented and depicted herein.

The foregoing description is considered as illustrative only of the principles of the invention, and since numerous modifications and changes will readily occur to those skilled in the art, it is not the inventor's desire to limit the invention to the exact construction and operation shown and described herein. Accordingly, all suitable modifications and equivalents may be resorted to, falling within the scope of the present invention.

I claim:

1. A method for alleviating a medical condition in a human in need of such treatment comprising:

applying an acupressure device on a selected skin surface portion of the human, the device comprising:

a thin flexible base sheet having a first side, a second side and a margin, the margin having at least a portion shaped as an orienting margin, wherein the orienting margin is shaped to correspond to a shape on or adjacent to the selected skin surface portion when the base sheet is placed on the selected body surface;

an adhesive layer on the first side of the base sheet suitable for the attaching the base sheet to the selected skin surface portion; and at least one bead on the adhesive layer suitable for positioning against the selected body surface for providing acupressure to at least a portion of the selected body surface.

2. The method of claim 1 wherein the flexible base sheet comprises a synthetic polymeric film.

3. The method of claim 1 wherein the flexible base sheet comprises synthetic polymeric fibers in a woven fabric.

4. The method of claim 1 wherein the flexible base sheet comprises natural fibers in a woven fabric.

5. The method of claim 1 wherein the at least one bead comprises a metal or metal alloy.

6. The method of claim 5 wherein the metal or metal alloy is selected from the group consisting of iron, stainless steel, nickel, copper, tin, zinc, platinum, gold, and silver.

7. The method of claim 1 wherein the at least one bead comprises a polymeric compound.

8. The method of claim 1 wherein the at least one bead comprises a ceramic compound.

9. The method of claim 1 wherein the at least one bead comprises a glass compound.

10. The method of claim 1 wherein the at least one bead comprises a rubber compound.

11. The method of claim 1 wherein the device further comprises a medicament suitable for topical and transdermal application to the selected skin surface portion.

12. The method of claim 11 wherein the medicament is a layer.

13. The method of claim 11 wherein the medicament is mixed into the base sheet.

14. The method of claim 11 wherein the medicament is camphor, tiger balm, or wintergreen.

15. The method of claim 1 wherein the medical condition is a headache, nausea, menstrual cramps, lower back pain, dental analgesia, a disorder associated with the back of the head, or a disorder associated with the back of the spine.

16. The method of claim 1 wherein the selected skin surface portion of a human body is an ear, hand, or sole of the foot.

17. The method of claim 1, wherein the medical condition is menstrual cramps.

18. A method for treating a headache in a human comprising:

applying an acupressure device on the human's antitragus, the device comprising a thin flexible base sheet having a first side, a second side and a margin, the margin having at least a portion shaped as an orienting margin, wherein the orienting margin is shaped to correspond to a shape on or adjacent to the antitragus when the base sheet is placed on the antitragus;

an adhesive layer on the first side of the base sheet suitable for attaching the base sheet to the antitragus; and at least one bead on the adhesive layer suitable for positioning against the antitragus for providing acupressure to the antitragus.

* * * * *

UNITED STATES PATENT AND TRADEMARK OFFICE
CERTIFICATE OF CORRECTION

PATENT NO. : 6,261,306 B1
DATED : July 17, 2001
INVENTOR(S) : Kramer

It is certified that error appears in the above-identified patent and that said Letters Patent is hereby corrected as shown below:

Column 5,
Line 22, delete "FIG. 4 therefore" and insert -- FIG. 4. --, therefor.
Line 23, delete "FIG. 4 therefore," and insert -- FIG. 4, --, therefor.
Line 30, delete "Orienting" and insert -- orienting --, therefor.

Column 7,
Line 34, delete "for the attaching" and insert -- for attaching --, therefor.
Line 39, after "surface" insert -- utilizing said orienting margin to position said at least one bead to a therapy point on said selected skin portion of the human --.

Column 8,
Line 45, after "antitragus" insert -- utilizing said orienting margin to position said at least one bead to a therapy point on the antitragus --.

Signed and Sealed this

Twenty-third Day of April, 2002

*Attest:*

JAMES E. ROGAN

*Attesting Officer* *Director of the United States Patent and Trademark Office*